United States Patent
Kerschner et al.

(10) Patent No.: US 6,858,217 B2
(45) Date of Patent: *Feb. 22, 2005

(54) STABILIZATION OF TERPENOIDS IN COSMETIC COMPOSITIONS

(75) Inventors: Judith Lynne Kerschner, Hawthorne, NJ (US); Arthur Ray Love, Nutley, NJ (US); Michael James Barratt, Oak Ridge, NJ (US)

(73) Assignee: Unilever Home & Personal Care USA division of Conopco, Inc., Greenwich, CT (US)

(*) Notice: Subject to any disclaimer, the term of this patent is extended or adjusted under 35 U.S.C. 154(b) by 50 days.

This patent is subject to a terminal disclaimer.

(21) Appl. No.: 10/386,258

(22) Filed: Mar. 11, 2003

(65) Prior Publication Data

US 2003/0185867 A1 Oct. 2, 2003

Related U.S. Application Data

(60) Provisional application No. 60/366,689, filed on Mar. 22, 2002.

(51) Int. Cl.$^7$ .............................. A61K 7/00; A61K 7/42; A61K 7/44
(52) U.S. Cl. ........................... 424/401; 424/59; 424/60; 424/400
(58) Field of Search ........................... 424/59, 60, 70.1, 424/400, 401

(56) References Cited

U.S. PATENT DOCUMENTS

| | | |
|---|---|---|
| 4,919,934 A | 4/1990 | Deckner et al. |
| 4,959,393 A | 9/1990 | Torihara et al. |
| 5,147,037 A | 9/1992 | Gardlick et al. |
| 5,188,831 A | 2/1993 | Nicoll et al. |
| 5,219,558 A | 6/1993 | Woodin, Jr. et al. |
| 5,961,961 A | 10/1999 | Dobrowski et al. |

FOREIGN PATENT DOCUMENTS

| | | |
|---|---|---|
| GB | 1581428 | 12/1980 |
| JP | 63 048209 | 2/1988 |
| JP | 02-292213 | 12/1990 |
| JP | 03 217299 | 9/1991 |
| JP | 04-169511 | 6/1992 |
| JP | 04-169516 | 6/1992 |
| JP | 05-004905 | 1/1993 |
| JP | 2000 016917 | 1/2000 |

OTHER PUBLICATIONS

*International Search Report* No. PCT/EP 03/02658 dated Jun. 27, 2003, 3 pp.
Patent Abstracts of Japan vol. 2000, No. 04, Aug. 31, 2000—abstract of JP 2000 016917.
Database WPI Derwent XP002244575—abstract of 63 048209.
Database WPI Derwent XP002244576—abstract of JP 03 217299.
Arctander, S., *Perfume and Flavor Chemicals*, vol. I and vol. II, Allured Pub. Co. (1969).
Bauer, K. et al., *Common Fragrance and Flavor Materials*, VCH Publishers (1990).
Muller, P.M. et al., (Eds.) *Perfumes: Art, Science, and Technology*, Elsevier Applied Science.
Lille, et al., *On Synthesis of 4–Substituted Alkyl Resorcins and Their IR Spectra*, Tr. Nauch–Issled., Inst. Slantsev, No. 18:127–134 (1969).
Love et al. To be assigned, Stabilization of Sunscreens in Cosmetic Compositions.
Love et al. To be assigned Stabilization of Resorcinol Derivatives in Cosmetic Compositions.

*Primary Examiner*—Shelley A. Dodson
(74) *Attorney, Agent, or Firm*—Ellen Plotkin

(57) ABSTRACT

Cosmetic compositions containing terpenoids along with a 4-substituted resorcinol derivative exhibit improved storage stability and oxidative stability.

11 Claims, No Drawings

STABILIZATION OF TERPENOIDS IN COSMETIC COMPOSITIONS

This application claims priority under 35 U.S.C. Section 119 from U.S. provisional application Ser. No. 60/366,689 filed Mar. 22, 2002.

FIELD OF THE INVENTION

The invention relates to cosmetic compositions containing terpenoids stabilized by 4-substituted resorcinol derivatives for use in personal care and personal wash products.

BACKGROUND OF THE INVENTION

Terpenes are widespread in nature, mainly in plants as constituents of essential oils. Many terpenes are hydrocarbons, but oxygen-containing compounds such as alcohols, aldehydes or ketones (terpenoids) are also found. Their building block is the hydrocarbon isoprene, $CH_2=C(CH_3)-CH=CH_2$ (isoprene rule, Wallach 1887). Terpene hydrocarbons therefore have molecular formulas $(C_5H_8)_n$, they are classified according to the number of isoprene units:

| number of isoprene units | |
| --- | --- |
| monoterpenes | 2 |
| sesquiterpenes | 3 |
| diterpenes | 4 |
| triterpenes | 6 |
| tetraterpenes | 8 |

Examples of monoterpenes are: pinene, nerol, citral, camphor, geraniol, limonene. Examples of sesquiterpenes are: nerolidol, farnesol. Examples of diterpenes are: vitamin $A_1$ (retinol). Squalene is an example of a triterpene, and carotene (provitamin $A_1$) is a tetraterpene.

The term "terpenoid", for purposes of the present invention, is intended to cover terpenes and derivatives thereof having at least one $C_5H_8$ hydrocarbon unit with one or more points of unsaturation within the chemical structure.

Terpenoids are useful organic compounds in many industries, particularly in resins, perfumes, fragrances, etc. Terpenoids are a fragrance raw material of many perfumes and scents. Fragrance terpenoids are disclosed in Arctander, S., *Perfume and Flavor Chemicals*, Vol. I and II, Allured Pub. Co. (1969) and examples include Ambregris odor chemicals, Jasmones, Musks, Pyran-derivatives, and Sandalwood fragrance chemicals.

It is well known that mixtures of perfume or fragrance raw materials when deposited on a surface or when incorporated in a cosmetic composition lose intensity and may change character with time, due to many factors. Many attempts have been made to minimize these drawbacks, but so far with minimal success. For example, Gardlick et al, U.S. Pat. No. 6,147,037 relates to fragrance delivery systems useful in delivering sustained or enduring fragrances to personal care items.

One factor responsible for loss of fragrance intensity or change in character is that terpenes are oxidatively unstable. The degree of oxidative instability depends on the degree of unsaturation, or the number of double or triple bonds in the organic compound.

Oxidative instability is an undesirable characteristic in terpenoids. There is a need, therefore, for an agent that will stabilize terpenoids against oxidation. In particular, there is a need for an agent that will prevent the oxidation of terpenoids which have at least one double bond in its chemical structure.

SUMMARY OF THE INVENTION

The present invention includes a personal care composition comprising:

a. about 0.000001 to about 10% of an unsaturated terpenoid, b. about 0.000001 to about 10% of a 4-substituted resorcinol derivative, and c. a vehicle or carrier.

The 4-substituted resorcinol derivatives include 4-linear alkyl resorcinols, 4-branched alkyl resorcinols, 4-cycloalkyl resorcinols, and mixtures thereof. Preferred resorcinol derivatives include 4-ethyl resorcinol, 4-isopropyl resorcinol, 4-butyl resorcinol, 4-cyclopentyl resorcinol and 4-cyclohexyl resorcinol, as well as acylated versions thereof.

The inventive compositions are aesthetically pleasing and have improved storage/oxidative stability.

DETAILED DESCRIPTION OF THE INVENTION

As used herein, the term "cosmetic composition" is intended to describe compositions for topical application to human skin, including leave-on and wash-off products.

The term "skin" as used herein includes the skin on the face, neck, chest, back, arms, axillae, hands, legs, and scalp.

As used herein, the term "unsaturation" is intended to describe an organic compound having double or triple bonds, such as an olefin or an alkyne.

The term "fragrance" is intended to mean one, but preferably two, or more fragrance raw materials which are artfully combined to impart a pleasurable scent, odor, essence, or fragrance characteristic.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

For the avoidance of doubt the word "comprising" is intended to mean including but not necessarily consisting of or composed of. In other words the listed steps or options need not be exhaustive.

We have now found that 4-substituted resorcinol derivatives inhibit the oxidation of unsaturated terpenoids. Preferably, in accordance with the present invention, 4-substituted resorcinols are used to stabilize unsaturated terpenoids incorporated in cosmetic compositions.

Resorcinol derivatives are known compounds and can be readily obtained, for example, by a method wherein a saturated carboxylic acid and resorcinol are condensed in the presence of zinc chloride and the resultant condensate is reduced with zinc amalgam/hydrochloric acid (Lille. J. Bitter, L A. Peiner. V, Tr. Nauch-Issled. Inst. slantsev 1969, No. 18, 127), or by a method wherein resorcinol and a corresponding alkyl alcohol are reacted in the presence of an alumina catalyst at a high temperature of from 200 to 400° C. (British Patent No. 1,581,428).

The inventive compositions generally contain about 0.000001 to about 50% of unsaturated terpenoids and about 0.000001 to about 50% of 4-substituted resorcinols. The particular advantage of the inventive compositions is that terpenoids can be stabilized by 4-substituted resorcinols against oxidation.

Terpenoids

Terpenoids, for purposes of the present invention, are terpenes and derivatives thereof having at least one $C_5H_8$ hydrocarbon unit with one or more points of unsaturation within the chemical structure. Fragrance terpenoids are described in Bauer, K., et al., *Common Fragrance and Flavor Materials*, VCH Publishers (1990).

Terpenoids that may be incorporated in the inventive cosmetic compositions are divided into three classes, including acyclic terpenoids, cyclic terpenoids, and cycloaliphatic compounds that are structurally related to terpenoids.

Terpene derivatives within each of the three classes include alcohols, ethers, aldehydes, acetals, acids, ketones, esters, and terpene compounds that contain heteroatoms such as nitrogen or sulfur.

Examples of terpenoids that may be incorporated in the cosmetic compositions of the present invention are set forth in the tables below:

TABLE 1

Acyclic Terpenoids

HYDROCARBONS

Myrcene
Ocimene
beta-Farnesene

ALCOHOLS

| | |
|---|---|
| Dihydromyrcenol | (2,6-dimethyl-7-octen-2-ol) |
| Geraniol | (3,7-dimethyl-trans-2,6-octadien-1-ol) |
| Nerol | (3,7-dimethyl-cis-2,6-octadien-1-ol) |
| Linalool | (3,7-dimethyl-1,6-octadien-3-ol) |
| Myrcenol | (2-methyl-6-methylene-7-octen-2-ol) |
| Lavandulol | |
| Citronellol | (3,7-dimethyl-6-octen-1-ol) |
| Trans-trans-Farnesol | (3,7,11-trimethyl-2,6,10-dodecatrien-1-ol) |
| Trans-Nerolidol | (3,7,11-trimethyl-1,6,10-dodecatrien-3-ol) |

ALDEHYDES AND ACETALS

| | |
|---|---|
| Citral | (3,7-dimethyl-2,6-octadien-1-al) |
| Citral diethyl acetal | (3,7-dimethyl-2,6-octadien-1-al diethyl acetal) |
| Citronellal | (3,7-dimethyl-6-octen-1-al) |
| Citronellyloxyacetaldehyde | |
| 2,6,10-Trimethyl-9-undecenal | |

KETONES

Tagetone
Solanone
Geranylacetone (6,10-dimethyl-5,9-undecadien-2-one)

ACIDS AND ESTERS

Cis-Geranic acid
Citronellic acid
Geranyl Esters, including Geranyl formate, Geranyl acetate, Geranyl propionate,
Geranyl isobutyrate, Geranyl isovalerate
Neryl Esters, including Neryl acetate
Linalyl Esters, including Lynalyl formate, Linalyl acetate, Linalyl propionate, Linalyl butyrate, Linalyl isobutyrate,
Lavandulyl Esters, including Lavendulyl acetate
Citronellyl Esters, including Citronellyl formate, Citronellyl acetate, Citronellyl propionate, Citronellyl isobutyrate, Citronellyl isovalerate,
Citronellyl tiglate

NITROGEN CONTAINING UNSATURATED TERPENE DERIVATIVES

Cis-Geranic acid nitrile
Citronellic acid nitrile

TABLE 2

Cyclic Terpenoids

HYDROCARBONS

| | |
|---|---|
| Limonene | (1,8-p-menthadiene) |
| Alpha-Terpinene | |
| Gamma-Terpinene | (1,4-p-menthadiene) |
| Terpinolene | |
| Alpha-Phellandrene | (1,5-p-menthadiene) |
| Beta-Phellandrene | |
| Alpha-Pinene | (2-pinene) |
| Beta-Pinene | (2(10)-pinene) |
| Camphene | |
| 3-Carene | |
| Caryophyllene | |
| (+)-Valencene | |
| Thujopsene | |
| Alpha-Cedrene | |
| Beta-Cedrene | |
| Longifolene | |

ALCOHOLS AND ETHERS

| | |
|---|---|
| (+)-Neoiso-isopulegol | |
| Isopulegol | (8-p-menten-3-ol) |
| Alpha-Terpineol | (1-p-menten-8-ol) |
| Beta-Terpineol | |
| Gamma-Terpineol | |
| Delta-Terpineol | |
| 1-Terpinen-4-ol | (1-p-menten-4-ol) |

ALDEHYDES AND KETONES

| | |
|---|---|
| Carvone | (1,8-p-mantadien-6-one) |
| Alpha-Ionone | $(C_{13}H_{20}O)$ |
| Beta-Ionone | $(C_{13}H_{20}O)$ |
| Gamma-Ionone | $(C_{13}H_{20}O)$ |
| Irone, alpha-, beta-, gamma- | $(C_{14}H_{22}O)$ |
| n-Methylionone, alpha-, beta-, gamma- | $(C_{14}H_{22}O)$ |
| Isomethylionone, alpha-, beta-, gamma- | $(C_{14}H_{22}O)$ |
| Allylionone | $(C_{16}H_{24}O)$ |
| Pseudoionone | |
| n-Methylpseudoionone | |
| Isomethylpseudoionone | |
| Damascones Including beta-Damascenone | 1-(2,6,6-trimethylcyclohexenyl)-2-buten-1-ones 1-(2,6,6-trimethyl-1,3-cyclohadienyl)-2-buten-1-one |
| Nootkatone | 5,6-dimethyl-8-isopropenylbicyclo[4.4.0]-1-decen-3-one |
| Cedryl methyl ketone | $(C_{17}H_{26}O)$ |

ESTERS

| | |
|---|---|
| Alpha-Terpinyl acetate | (1-p-menthen-8-yl acetate) |
| Nopyl acetate | (-)-2-(6,6-dimethylbicyclo[3.1.1]hept-2-en-2-yl)ethyl acetate |
| Khusymil acetate | |

TABLE 3

Cycloaliphatic Compounds Structurally Related to Terpenes

ALCOHOLS

5-(2,2,3-Trimethyl-3-cyclopenten-1-yl)-3-methylpentan-2-ol

ALDEHYDES

2,4-Dimethyl-3-cyclohexene carboxaldehyde
4-(4-Methyl-3-penten-1-yl)-3-cyclohexene carboxaldehyde
4-(4-Hydroxy-4-methypentyl)-3-cyclohexene carboxaldehyde

KETONES

| | |
|---|---|
| Civetone | |
| Dihydrojasmone | (3-methyl-2-pentyl-2-cyclopenten-1-one) |
| Cis-Jasmone | 3-methyl-2-(2-cis-penten-1-yl)-2-cyclopenten-1-one |

TABLE 3-continued

Cycloaliphatic Compounds Structurally Related to Terpenes

5-Cyclohexadecen-1-one
2,3,8,8-Tetramethyl-1,2,3,4,5,6,7,8-octahydro-2-napthalenyl methyl ketone
3-methyl-2-cyclopenten-2-ol-1-one
ESTERS 4,7-Methano-3a,4,5,6,7,7a-hexahydro-5-(or 6)-indenyl acetate
Allyl 3-cyclohexylpropionate
Methyl dihydrojasmonate methyl (3-oxo-2-pentylcyclopentyl)acetate Preferably, the amount of terpenoid in the cosmetic composition is in the range of about 0.000001% to about 10%, more preferably about 0.00001% to about 5 wt %, most preferably about 0.0001% to about 2%.

As discussed above, one factor responsible for loss of fragrance intensity or change in character is that the unsaturated terpenes are oxidatively unstable.

4-Substituted Resorcinols

The stability of the inventive compositions is achieved by the use of an antioxidant agent which comprises, as an effective component, a resorcinol derivative of the following formula (I):

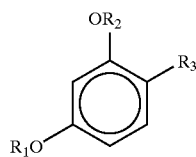

(I)

Each $R_1$ and $R_2$, independently, represents a hydrogen atom, —CO—R (acyl group), —COO—R, CONHR; the latter three represented by the following formula A, respectively:

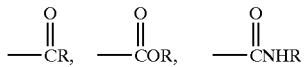

(A)

where R represents saturated or unsaturated, linear branched or cyclic $C_1-C_{18}$ hydrocarbon. In a preferred embodiment, each or both $R_1$ and/or $R_2$ represents hydrogen. In a more preferred embodiment, both $R_1$ and $R_2$ represent hydrogen. $R_3$ represents:

(1) saturated or unsaturated, linear branched or cyclic $C_1-C_{18}$ hydrocarbon, preferably a $C_2-C_{12}$ hydrocarbon; or (2) a group of general formula (II) (II)

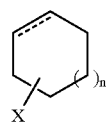

(II)

Wherein X is hydrogen; $OR^1$, wherein $R^1$ represents hydrogen, $(C_1-C_6)$alkyl or aryl-$(C_1-C_6)$alkyl; $OCOR^2$ wherein $R^2$ represents $(C_1-C_6)$alkyl, aryl-$(C_1-C_6)$alkyl or phenyl; halogen; $(C_1-C_6)$alkyl; aryl-$(C_1-C_6)$alkyl, or aryl-$(C_1-C_6)$alkyl; or $NHR^1$ wherein $R^1$ is defined as above; wherein n is 0 to 3; and wherein the dashed line indicates an optional double bond.

For example, where n is 0, the group of general formula II is a 5-member ring; where n is 1, the group is a 6-member ring; where n is 2, a 7-member ring; and where n is 3, an 8 member ring.

4-Substituted Resorcinols: Linear or Branched

In the above formula (1), the group represented by $R_3$ and preferably having from 2 to 12 carbon atoms, where the arrangement is linear, may include an ethyl group, a propyl group, a butyl group, a pentyl group, a hexyl group, a heptyl group, an octyl group, a nonyl group, a decyl group, an undecyl group and a dodecyl group. These linear alkyl groups may be substituted with a methyl or ethyl group at one or more hydrogen atoms thereof. Specific examples of the substituted alkyl group include an isopropyl group, an isobutyl group, an isoamyl group, a 2-methylhexyl group and the like. Preferred alkyl groups are those where $R_3$ is an ethyl, propyl, isopropyl, butyl, pentyl, hexyl, heptyl, or octyl group. The most preferable alkyl resorcinols are those where $R_3$ is an ethyl, isopropyl, butyl or hexyl group.

4-Cycloalkyl Resorcinols

In the case resorcinol derivatives of formula (I) where $R_3$ represents a structure of the general formula (II) shown hereinabove, the resorcinol derivatives are referred to herein as 4-cycloalkyl resorcinols, and are represented by the general formula (III):

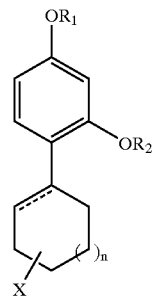

(III)

In the general formula (III) (as well as formula (II) hereinabove):

X represents hydrogen; $OR^1$, wherein $R^1$ represents hydrogen, $(C_1-C_6)$alkyl or aryl-$(C_1-C_6)$alkyl; $OCOR^2$ wherein $R^2$ represents $(C_1-C_6)$alkyl, aryl-$(C_1-C_6)$alkyl or phenyl; halogen; $(C_1-C_6)$alkyl; aryl-$(C_1-C_6)$alkyl, or aryl-$(C_1-C_6)$alkyl; or $NHR^1$ wherein $R^1$ is defined as above;

n is 0 to 3; and the dashed line indicates an optional double bond at that position.

Examples of more specific embodiments of the 4-cycloalkyl resorcinols include:

(a) compounds of the formula (III) wherein a single bond connects the two carbon atoms at the dashed line;

(b) compounds of the formula (III) wherein n is one;

(c) compounds of the formula (III) wherein X is hydrogen;

(d) compounds of the formula (III) wherein X is hydrogen, methyl or ethyl;

(e) compounds of the formula (III) wherein n is zero;

(f) compounds of the formula (III) wherein n is two; and (g) compounds of the formula (III) wherein X is benzyloxy.

Preferred compounds of formula (III) are 4-cyclopentyl resorcinol, 4-cyclohexyl resorcinol, 4-cycloheptyl resorcinol, and 4-cyclooctyl resorcinol. Most preferred compounds of formula (III) are 4-cyclohexyl resorcinol and 4-cyclopentyl resorcinol.

An amount of 4-substituted resorcinol derivative effective to inhibit the oxidation of unsaturated terpenoids may be determined by experimentation. The unsaturated terpenoids and 4-substituted resorcinol derivatives are present in the composition in a weight ratio of 1:10000 to 10000:1 of terpene:resorcinol, preferably 1:1000 to 1:5000, more preferably 1:1 to 1:1000.

The amount of the resorcinol derivative is in the range of about 0.00001% to about 10%, preferably about 0.001 to about 7%, most preferably about 0.01 to about 5%, of the total amount of a cosmetic composition.

Skin Benefit Agents

The cosmetic compositions of the present invention may be used in personal care and personal wash products, such as, for example, lotions, soaps, deodorants, etc. The terpenoid compounds and the stabilizing agents that form the compositions of the present invention may have other useful functions when incorporated in personal care compositions.

Preferred personal care compositions are those suitable for the application to human skin, which optionally, but preferably, include a skin benefit agent. Suitable skin benefit agents include anti-aging, wrinkle-reducing, skin whitening, anti-acne, and sebum reduction agents. Examples of these include alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives other than the 4-substituted resorcinol derivatives discussed hereinabove (thereby serving a dual function of oxidative terpenoid stability and skin benefit such as for acne, skin lightening, or for hair treatment).

Cosmetically Acceptable Vehicle

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferentially oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces skin dryness and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. For leave-on products, total concentration of the surfactant will range from 0.1 to 40%, preferably from 1 to 20%, optimally from 1 to 5% by weight of the composition. For wash-off products, such as cleansers and soap, total concentration of surfactant will range at about 1 to about 90%. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

The inventive cosmetic compositions optionally contain a lathering surfactant. By a "lathering surfactant" is meant a surfactant which, when combined with water and mechanically agitated, generates a foam or lather. Preferably, the lathering surfactant should be mild, meaning that it must provide sufficient cleansing or detergent benefits but not overly dry the skin, and yet meet the lathering criteria described above. The cosmetic compositions of the present invention may contain a lathering surfactant in a concentration of about 0.01% to about 50%.

Optional Components

To the ordinarily employed cosmetic bases may be added UV absorbers, UV diffusing agents typical of which is finely divided titanium oxide, various other plasticizers, elastomers, calamine, pigments, antioxidants, chelating agents, and perfumes.

Other adjunct minor components may also be incorporated into the inventive cosmetic compositions. These ingredients may include coloring agents, opacifiers, and perfumes. Amounts of these other adjunct minor components may range anywhere from 0.001% up to 20% by weight of the composition.

The following specific examples further illustrate the invention, but the invention is not limited thereto. In all examples, terpenoids were obtained from Aldrich Chemicals.

EXAMPLE 1

Cosmetic compositions within the scope of the invention were prepared.

A base formulation shown in the Table below was made by heating phase A ingredients to 70 to 85° C. with stirring. Phase B ingredients were heated in a separate container to 70 to 85° C. with stirring. Then, phase A was added into phase B while both phases were kept at 70 to 85° C. The mixture was stirred for at least 15 minutes at 70 to 85° C., then cooled. Phase C ingredients were added at 50° C., followed by Phase D ingredients added at 40° C.

A base formulation is shown in the table below.

TABLE 4

| Ingredients | a % wt. | b % wt. | Phase |
| --- | --- | --- | --- |
| Isostearyl Palmitate | 6.00 | 6.00 | A |
| C12–C15 Alkyl Octanoate | 3.00 | 3.00 | A |
| PEG-100 Stearate | 2.00 | 2.00 | A |
| Glyceryl Hydroxystearate | 1.50 | 1.50 | A |
| Stearyl Alcohol | 1.50 | 1.50 | A |
| Stearic acid | 3.00 | 4.00 | A |
| TEA, 99% | 1.20 | 1.20 | B |
| Dimethicone | 1.00 | 1.00 | A |
| Sorbitan Monostearate | 1.00 | 1.00 | A |
| Magnesium Aluminum Silicate | 0.60 | 0.60 | B |
| Vitamin E acetate | 0.10 | 0.10 | A |
| Cholesterol | 0.50 | 0.50 | A |
| Simethicone | 0.01 | 0.01 | B |
| Xanthan gum | 0.20 | 0.20 | B |
| Hydroxyethylcellulose | 0.50 | 0.50 | B |
| Propylparaben | 0.10 | 0.10 | A |
| Disodium EDTA | 0.05 | 0.05 | B |
| Fragrance components (other than terpenoid) | 0.50 | 0.50 | D |
| Niacinamide | 0.05 | 0.05 | C |
| BHT | 0.10 | 0.10 | C |
| 4-ethyl resorcinol | 0.05 | 2.00 | C |
| Santalal (Terpenoid) | 0.0005 | 0.001 | D |
| Methylparaben | 0.15 | 0.15 | B |
| Water | BAL | BAL | B |
| Total | 100.00 | 100.00 | B |

EXAMPLE 2

An additional cosmetic composition was prepared falling within the scope of the invention.

TABLE 5

| | Wt % | Phase |
| --- | --- | --- |
| water, DI | BAL | A |
| disodium EDTA | 0.05 | A |
| magnesium aluminum silicate | 0.6 | A |
| methyl paraben | 0.15 | A |
| simethicone | 0.01 | A |
| butylene glycol 1,3 | 3.0 | A |
| hydroxyethylcellulose | 0.5 | A |
| glycerine; USP | 2.0 | A |
| xanthan gum | 0.2 | A |
| triethanolamine | 1.2 | B |
| stearic acid | 3.0 | B |
| propyl paraben NF | 0.1 | B |
| glyceryl hydroxystearate | 1.5 | B |
| stearyl alcohol | 1.5 | B |
| isostearyl palmitate | 6.0 | B |
| C12–15 alcohols octanoate | 3.0 | B |
| dimethicone | 1.0 | B |
| cholesterol NF | 0.5 | B |
| sorbitan stearate | 1.0 | B |
| Non-terpenoid Fragrance components | 1.0 | B |

TABLE 5-continued

|  | Wt % | Phase |
|---|---|---|
| tocopheryl acetate | 0.1 | B |
| PEG-100 stearate | 2.0 | B |
| sodium stearoyl lactylate | 0.5 | B |
| hydroxycaprylic acid | 0.1 | C |
| 4-cyclohexyl resorcinol | 10.0 | C |
| linalool | 0.001 | D |
| BHT | 0.10 | C |
| Niacinamide | 0.05 | C |
| alpha-bisabolol | 0.2 | C |

The composition of Example 2, was prepared as follows:
1. Heat Phase A to 80° C. while mixing.
2. Heat Phase B to 75° C. in a separate container while mixing.
3. Add B to A and mix with heat maintained at 70–80° C. for 15 min. and then heat turned off and continued mixing for another 15 min.
4. At 50° C. add Phase C and mix for 10 min.
5. At 40° C. add Phase D and mix for 10 min.

EXAMPLES 3–10

A set of additional compositions within the scope of the present invention were prepared by the method of Example 1 and are listed in the table below.

TABLE 6

| Ingredients | Phase | 3 acid soap base | 4 | 5 | 6 | 7 | 8 | 9 | 10 |
|---|---|---|---|---|---|---|---|---|---|
| Stearic acid | A | 17.9 | 17.9 | 17.9 | 17.9 | 17.9 | 17.9 | 17.9 | 17.9 |
| Sodium cetearyl sulfate | A |  | 2.2 |  | 1 | 1.5 | 2 | 3 | 2 |
| Myrj 59 | A |  |  |  | 2 | 2 | 2 | 2 | 1 |
| Propylparaben | A | 0.1 | 0.1 | 0.1 | 0.1 | 0.1 | 0.1 | 0.1 | 0.1 |
| Disodium EDTA | A | 0.05 | 0.05 | 0.05 | 0.05 | 0.05 | 0.05 | 0.05 | 0.05 |
| Span 60 | A |  |  | 2 | 2 | 2 | 2 | 2 | 1 |
| BHT | C | 0.10 | 0.10 | 0.10 | 0.10 | 0.10 | 0.10 | 0.10 | 0.10 |
| 4-butyl resorcinol | C | 0.05 | 0.05 | 2.0 | 2.0 | 3.5 | 3.5 | 5.0 | 10.0 |
| Limonene and Linalool mixture | D | 0.001 | 0.001 | 0.01 | 0.01 | 0.5 | 0.5 | 0.001 | 0.01 |
| KOH, 22% | B | 2.20 |  |  |  |  |  |  |  |
| Glycerin | B | 1 | 1 | 1 | 1 | 1 | 1 | 1 | 1 |
| Methylparaben | B | 0.15 | 0.15 | 0.15 | 0.15 | 0.15 | 0.15 | 0.15 | 0.15 |
| Water | B | BAL | BAL | BAL | BAL | BAL | BAL | BAL | BAL |

EXAMPLE 11

The stability of terpenoid components of typical fragrances was examined in skin care formulations containing 4-substituted resorcinol derivatives to determine the resorcinol's effectiveness toward preventing degradation and loss of terpenoid upon storage. Two terpenoid components, limonene and linalool, were formulated as part of a fragrance in standard skin care lotions containing BHT (a standard antioxidant), unsubstituted resorcinol, 4-ethyl resorcinol and 4-hexyl resorcinol. The stability of these fragrance components was measured using GC/HS analysis to determine the loss of each terpenoid molecule with time as stored under typical consumer product storage conditions storage (5-month storage at 40° C. and in the sun at Room Temperature [RT]). The loss of limonene and linalool in a standard formulation containing no "anti-oxidants" was directly compared to loss of these materials with both BHT, unsubstituted resorcinol and the 4-substituted resorcinol derivatives. The formulations are presented in Table 7 and the stability data is presented in Table 8.

With reference to the data in the Tables below, GC/HS measurements were taken on an Agilent 6890 GC/5973 MS using a Gerstel MPS2 Headspace Sampler. The samples were incubated at 35° C. for one hour and then 2.50 mL of the headspace above the sample was injected onto a Agilent Technologies number 19091S-433, HP-5MS, 5% Phenyl Methyl Siloxane column which has a 30 m×0.25 mm ID with a 0.25 µm film thickness. The GC data is recorded as peak area count for the two fragrance components.

The formulations in the Table below were prepared in accordance with the method set forth in Example 1 hereinabove.

TABLE 7

Formulations for Skin Lotions

| Raw Material |  | #1 Wt % | #2 Wt % | #3 Wt % | #4 Wt % | #5 Wt % |
|---|---|---|---|---|---|---|
| Stearic acid | A | 17.90 | 17.90 | 17.90 | 17.90 | 17.90 |
| Cetostearyl Alcohol | A | 0.53 | 0.53 | 0.53 | 0.53 | 0.53 |
| Dimethicone (DC200, 350 cSt) | A | 0.50 | 0.50 | 0.50 | 0.50 | 0.50 |
| Parsol MCX | A | 1.25 | 1.25 | 1.25 | 1.25 | 1.25 |
| Parsol 1789 | A | 0.40 | 0.40 | 0.40 | 0.40 | 0.40 |
| Propyl paraben | A | 0.10 | 0.10 | 0.10 | 0.10 | 0.10 |

TABLE 7-continued

Formulations for Skin Lotions

| Raw Material |  | #1 Wt % | #2 Wt % | #3 Wt % | #4 Wt % | #5 Wt % |
|---|---|---|---|---|---|---|
| Water | B | 55.88 | 55.88 | 55.88 | 55.88 | 55.88 |
| Glycerin | B | 1.00 | 1.00 | 1.00 | 1.00 | 1.00 |
| EDTA | B | 0.04 | 0.04 | 0.04 | 0.04 | 0.04 |
| Methyl paraben | B | 0.20 | 0.20 | 0.20 | 0.20 | 0.20 |
| KOH, 22% | B | 2.20 | 2.20 | 2.20 | 2.20 | 2.20 |
| Fragrance (contains limonene 20% and linalool 20%). | D | 1.0 | 1.0 | 1.0 | 1.0 | 1.0 |
| Niacinamide | C | 1.00 | 1.00 | 1.00 | 1.00 | 1.00 |
| BHT | C | 0.10 | — | — | — | — |
| 4-Ethyl Resorcinol | C | — | 3.55 | — | — | — |

TABLE 7-continued

Formulations for Skin Lotions

| Raw Material | #1 Wt % | #2 Wt % | #3 Wt % | #4 Wt % | #5 Wt % |
|---|---|---|---|---|---|
| 4-Hexyl Resorcinol | C | — | — | 5.00 | — | — |
| Resorcinol | C | — | — | — | 2.84 | — |
| Q.S. to 100% with water | Q.S. | Q.S. | Q.S. | Q.S. | Q.S. |

TABLE 8

Stability of Limonene and Linalool in Formulations

| Formula # | | initial GC/HS | Sun 5-months GC/HS | % Loss | % Stabilization | 40° C. 5-months GC/HS | % Loss | % Stabilization |
|---|---|---|---|---|---|---|---|---|
| 5 | Control | | | | | | | |
| | Limonene | 51812033 | 36654323 | 29.2 | | 26830284 | 48.2 | |
| | Linalool | 8109405 | 5054708 | 37.6 | | 4878857 | 39.8 | |
| | BHT Sample | | | | | | | |
| | Limonene | 38342803 | 32465677 | 15.3 | 48 | 26286287 | 31.7 | 35 |
| | Linalool | 6853529 | 4678449 | 31.4 | 16.5 | 4918953 | 28.2 | 29 |
| 2 | 4-EthylResorcinol | | | | | | | |
| | Limonene | 54736538 | 54753996 | 0 | 100 | 46790409 | 12.9 | 74 |
| | Linalool | 3288967 | 2650924 | 19.4 | 49 | 2292953 | 30.2 | 25 |
| 3 | 4-HexylResorcinol | | | | | | | |
| | Limonene | 40778538 | 34662250 | 7.7 | 84 | 3381932 | 18.5 | 72 |
| | Linalool | 2222930 | 1666185 | 7.5 | 80 | 1466948 | 10.2 | 75 |
| 4 | Resorcinol | | | | | | | |
| | Limonene | 45478209 | 25743642 | 43.4 | 0 | 19260141 | 57.6 | 0 |
| | Linalool | 6088780 | 3856563 | 36.7 | 3 | 4286137 | 29.6 | 26 |

As shown by the data in the table above, the 4-substituted resorcinols are as efficient or even better in some cases as BHT toward stablizing these terpenoid molecules against degradation, with the unsubstituted resorcinol providing little to no stabilization of these fragrance components. In most cases, the "control" formulation without anti-oxidants or the control with the unsubstituted resorcinol lost twice as much limonene and/or linalool as those formulations containing the 4-substituted resorcinols. These results indicate a clear, additional benefit for terpenoid stability with the addition of 4-substituted resorcinols.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A personal care composition comprising:
   a. about 0.000001 to about 10% of an unsaturated terpenoid;
   b. about 0.000001 to about 10% of a 4-substituted resorcinol derivative of the general formula (I):

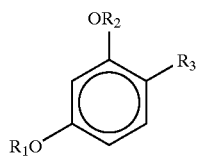

(I)

wherein each $R_1$ and $R_2$ independently is selected from the group consisting of a hydrogen atom, —CO—R, —COO—R, and CONHR; wherein R represents a $C_1$–$C_{18}$ hydrocarbon;

$R_3$ represents a $C_1$–$C_{18}$ hydrocarbon or has a general formula (II):

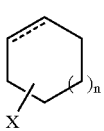

(II)

wherein X represents hydrogen; $OR^1$, wherein $R^1$ represents hydrogen, $(C_1$–$C_6)$alkyl or aryl-$(C_1$–$C_6)$alkyl; $OCOR^2$ wherein $R^2$ represents $(C_1$–$C_6)$alkyl, aryl-$(C_1$–$C_6)$ alkyl or phenyl; halogen; $(C_1$–$C_6)$alkyl; aryl- ($C_1$–$C_6$)alkyl, or aryl-($C_1$–$C_6$)alkyl; or $NHR^1$ wherein $R^1$ is defined as above;

n is 0 to 3; and the dashed line indicates an optional double bond; and c. a cosmetically acceptable vehicle.

2. The composition of claim 1, wherein said terpenoid is selected from the group consisting of acyclic terpenoids, cyclic terpenoids, cycloaliphatic compounds that are structurally related to terpenoids, and mixtures thereof.

3. The composition of claim 2 wherein said terpenoids comprise terpenes and terpene derivatives selected from the group consisting of alcohols, aldehydes, acetals, ketones, acids, esters, and terpene compounds that contain heteroatoms selected from the group consisting of nitrogen or sulfur, and mixtures thereof.

4. The composition of claim 2 wherein said acyclic terpenoids are selected from the group consisting of Myrcene, Ocimene, beta-FameSene, Dihydromyrcenol, Geraniol, Nerol, Linalool, Myrcenol, Lavandulol, Citronellol, Trans-trans-Farnesol, Trans-Nerolidol, Citral, Citral diethyl acetal, Citronellal, Citronellyloxyacetaldehyde, 2,6,10-Trimethyl-9-undecenal, Tagetone, Solanone, Geranylacetone, Cis-Geranic acid Citronellic acid, Geranyl formate, Geranyl acetate, Geranyl propionate, Geranyl isobutyrate, Geranyl isovalerate, Neryl acetate, Lynalyl formate, Linalyl acetate, Linalyl propionate, Linalyl butyrate, Linalyl isobutyrate, Lavendulyl acetate, Citronellyl formate, Citronellyl acetate, Citronellyl propionate, Citronellyl isobutyrate, Citronellyl isovalerate, Citronellyl tiglate, Cis-Geranic acid nitrile, Citronellic acid nitrile, and mixtures thereof.

5. The composition of claim 2 wherein said cyclic terpenoids are selected from the group consisting of Limonene, Alpha-Terpinene, Gamma-Terpinene, Terpinolene, Alpha-Phellandrene, Beta-Phellandrene, Alpha-Pinene, Beta-Pinene, Camphene, 3-Carene, Caryophytlene, (+)-Valencene, Thujopsene, Alpha-Cedrene, Beta-Cedrene, Longifolene, (+)-Neoiso-isopulegol, Isopulegol, Alpha-Terpineol, Beta-Terpineol, Gamma-Terpineol, Delta-Terpineol, 1-Terpinen-4-ol, Carvone, Alpha-lonone, Beta-lonone, Gamma-lonone, Alpha-Irone, beta-Irone, gamma-Irone, alpha-n-Methylionone, beta--n-Methylionone, gamma--n-Methylionone, alpha-Isomethylionone, beta--Isomethylionone, gamma--Isomethylionone, Allylionone, Pseudojonone, n-Methylpseudoionone, Isomethylpseudoionone, Damascones, beta-Damascenone, Nootkatone, Cedryl methyl ketone, Alpha-Terpinyl acetate, Nopyl acetate, Khusymil acetate, and mixtures thereof.

6. The composition of claim 2 wherein said cycloaliphatic compounds that are structurally related to terpenoids are selected from the group consisting of 5-(2,2,3-Trimethyl-3-cyclopenten-1-yl)-3-methylpentan-2-ol,2,4-Dimethyl-3-cyclohexene carboxaldehyde, 4-(4-Methyl-3-penten-1-yl)-3-cyclohexene carboxaldehyde, 4-(4-Hydroxy-4-methypentyl)-3-cyclohexene carboxaldehyde, Civetone, Dihydrojasmone, Cis-Jasmone, 5-Cyclohexadecen-1-one, 2,3,8,8-Tetramethyl-1,2,3,4,5,6,7,8-octahydro-2-napthalenyl methyl ketone, 3-methyl-2-cyclopenten-2-ol-1-one, 4,7-Methano-3a,4,5,6,7,7a-hexahydro-5-(or 6)-indenyl acetate, Allyl 3-cyclohexylpropionate, Methyl dihydrojasmonate methyl (3-oxo-2-pentylcyclopentyl)acetate, and mixtures thereof.

7. The composition of claim 1, wherein said 4-substituted resorcinol derivative is present in at least an effective amount to inhibit oxidation of said unsaturated terpenoid.

8. The composition of claim 1, wherein the 4-substituted resorcinol is selected from the group consisting of 4-linear alkyl resorcinols, 4-branched alkyl resorcinols, 4-cycloalkyl resorcinols, and mixtures thereof.

9. The composition of claim 1, wherein the wherein the 4-substituted resorcinol is selected from the group consisting of 4-methyl resorcinol, 4-ethyl resorcinol, 4-propyl resorcinol, and 4-butyl resorcinol, 4-pentyl resorcinol, 4-hexyl resorcinol, 4-heptyl resorcinol, 4-octyl resorcinol, 4-nonyl resorcinol, 4-decyl resorcinol, 4 cyclopentyl resorcinol, 4-cyclohexyl resorcinol, 4-cycloheptyl resorcinol, 4-cyclooctyl resorcinol, and mixtures thereof.

10. The cosmetic composition of claim 1, further comprising a skin benefit agent selected from the group consisting of alpha-hydroxy acids and esters, beta-hydroxy acids and esters, polyhydroxy acids and esters, kojic acid and esters, ferulic acid and ferulate derivatives, vanillic acid and esters, dioic acids and esters, retinol, retinal, retinyl esters, hydroquinone, t-butyl hydroquinone, resorcinol derivatives, and mixtures thereof.

11. A cosmetic composition comprising:

a. an unsaturated terpenoid stabilized by a 4-substituted resorcinol derivative;

b. a skin benefit agent; and c. a cosmetically acceptable vehicle;

wherein said terpenoid is present in an amount of about 0.0001 wt % to about 5 wt % of said cosmetic composition; and wherein the weight ratio of said terpenoid to said 4-substituted resorcinol derivative is about 10,000:1 to about 1:100,000.

* * * * *